United States Patent [19]

Joyce et al.

[11] Patent Number: 5,231,210
[45] Date of Patent: Jul. 27, 1993

[54] METHOD FOR MAKING AROMATIC CARBONATES

[75] Inventors: Richard P. Joyce, East Nassau; Joseph A. King, Jr., Schenectady; Eric J. Pressman, East Greenbush, all of N.Y.

[73] Assignee: General Electric Company, Schenectady, N.Y.

[21] Appl. No.: 929,749

[22] Filed: Aug. 17, 1992

[51] Int. Cl.⁵ .............................................. C07C 69/96
[52] U.S. Cl. ................................................... 558/274
[58] Field of Search ........................................ 558/274

[56] References Cited

U.S. PATENT DOCUMENTS

| | | | |
|---|---|---|---|
| 4,096,168 | 6/1978 | Hallgren | 558/268 |
| 4,096,169 | 6/1978 | Chalk | 558/268 |
| 4,221,920 | 9/1980 | Hallgren | 562/406 |
| 4,260,802 | 4/1981 | Hallgren | 560/71 |
| 5,142,086 | 8/1992 | King, Jr. et al. | 558/274 |

*Primary Examiner*—Jose G. Dees
*Assistant Examiner*—Dwayne C. Jones
*Attorney, Agent, or Firm*—William A. Teoli; William H. Pittman

[57] ABSTRACT

A method is provided for making diphenyl carbonate by the direct carbonylation of phenol utilizing a palladium catalyst in combination with an inorganic cocatalyst in the form of a cobalt pentadentate complex.

4 Claims, 1 Drawing Sheet

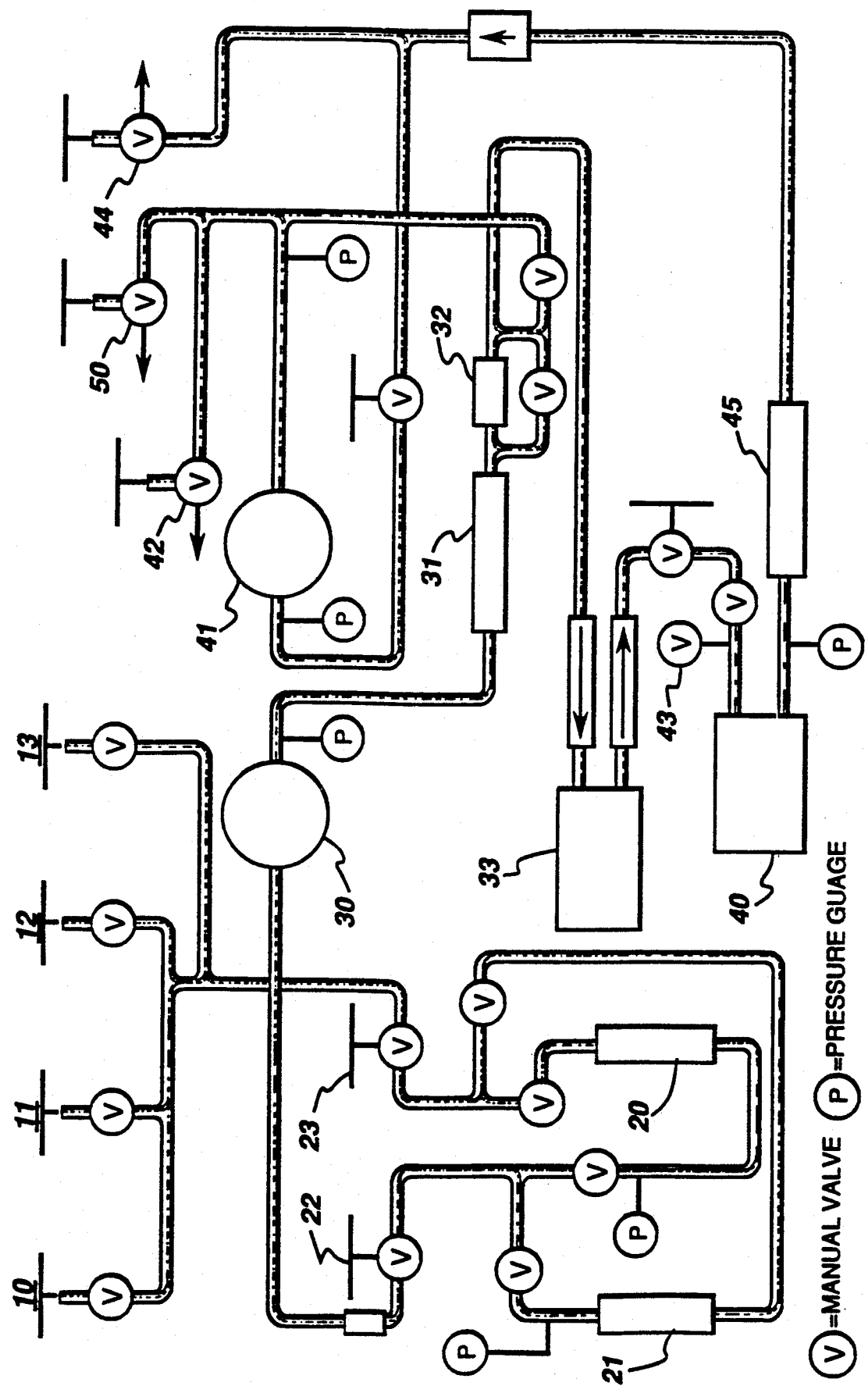

METHOD FOR MAKING AROMATIC CARBONATES

CROSS REFERENCE TO RELATED APPLICATIONS

Reference is made to copending applications Ser. Nos. 07/929,862, 07/929,861 and 07/929,860 filed on Aug. 17, 1992 filed concurrently herewith, and copending application Ser. No. 07/906,681, filed Jul. 7, 1992.

BACKGROUND OF THE INVENTION

The present invention relates to a method for making aromatic organic carbonates such as diphenyl carbonate by effecting reaction between an aromatic organic hydroxy compound, such as phenol, and carbon monoxide and oxygen in the presence of an effective amount of a palladium carbonylation catalyst. More particularly, the present invention relates to the carbonylation of an aromatic organic hydroxy compound utilizing an inorganic cocatalyst, such as a cobalt complex containing a pentadentate Schiff base in combination with the palladium catalyst.

Procedures for making diorganic carbonates are shown by Hallgren, U.S. Pat. Nos. 4,361,519 and 4,410,464, utilizing a molecular sieve as a drying agent for the water formed during the reaction. An additional carbonylation method for making diorganic carbonates is shown by Japanese patent 01,165,551. Aromatic organic carbonates are of particular interest to thermoplastic manufacturers, since they offer an alternative non-phosgene route to aromatic polycarbonates by melt transesterification. A procedure for making aromatic organic carbonates using an organic solvent, such as methylene chloride, is shown by Chalk, U.S. Pat. No. 4,187,242. Reference also is made to T. C. Chang in copending application Ser. No. 217,248, filed Jul. 11, 1988, and EP350-700-A, utilizing a divalent or trivalent manganese salt or cobalt (II) salt and hydroquinone in combination with a palladium catalyst, to catalyze the conversion of an aromatic organic hydroxy compound, such as phenol, to an aromatic organic carbonate. U.S. Pat. No. 4,218,391, Romano et al employs a copper salt to prepare organic esters of carbonic acid. Attempts to use such catalyst with aromatic organic hydroxy compounds, such as phenol, under constant flow conditions have been found to provide unsatisfactory results with respect to % carbonate yields and % carbonate selectivity as compared to the use of aliphatic hydroxy compounds, such as methanol, in preparing aliphatic carbonates under substantially the same conditions.

In application EP350-700-A and copending application Ser. No. 07/906,681, carbonylation of aromatic organic hydroxy compound was achieved utilizing a divalent or trivalent manganese salt or cobalt (II) salts and organic cocatalysts such as hydroquinone or benzoquinone in combination with a palladium catalyst. Although the aforementioned cocatalyst system provided improved yields of aromatic organic carbonate as a result of the carbonylation of aromatic organic hydroxy compounds, using inorganic cocatalyst, such as cobalt (II) salts, methods for achieving higher rates of aromatic organic carbonate production are constantly being evaluated. In addition, it is also known that a variety of organic cocatalysts can sometimes degrade after being used at elevated pressures and temperatures in a carbonylation reaction and then exposed to ambient conditions of pressure and temperature. Color bodies also can be formed in the reaction mixture.

SUMMARY OF THE INVENTION

The present invention is based on the discovery that certain cobalt complexes containing pentadentate Schiff base ligands can be substituted for cobalt (II) salts, and trivalent manganese salts as inorganic carbonylation cocatalyst. The resulting palladium carbonylation catalysts have been found to substantially enhance the rate of aromatic organic carbonate production. In addition, aromatic organic carbonate having reduced color bodies can be obtained using the cobalt complex containing a pentadentate Schiff base ligand as a palladium cocatalyst, since the resulting palladium carbonylation catalyst does not require the addition of an organic cocatalyst.

BRIEF DESCRIPTION OF THE DRAWING

The drawing shows a schematic of a gas flow reactor system for preparing aromatic carbonate.

STATEMENT OF THE INVENTION

There is provided by the present invention, a method for making aromatic organic carbonate comprising effecting reaction at a temperature of about 60° C. to about 150° C., between aromatic organic hydroxy compound, carbon monoxide and oxygen in the presence of an effective amount of a palladium carbonylation catalyst comprising, (a) catalytically active palladium in the metallic or chemically combined state,
(b) an inorganic catalyst in the form of a cobalt complex of a cobalt (II) salt and a material capable of forming a pentadentate ligand with the cobalt (II) salt, which material is a member selected from the class consisting of aromatic amines, aliphatic amines, aromatic ethers, aliphatic ethers, aromatic or aliphatic amine ethers, and Schiff bases, and
(c) quaternary ammonium or phosphonium halide.

The palladium material useful as a catalyst can be in elemental form, or it can be employed as a palladium compound. Accordingly, palladium black or elemental palladium deposited on carbon can be used as well as palladium compounds, such as halides, nitrates, carboxylates, oxides and complexes involving such compounds such as carbon monoxide, amines, phosphines or olefins. The preferred palladium compounds are palladium (II) salts or organic acids including carboxylates with $C_{(2-6)}$ aliphatic acids. Palladium (II) acetate is particularly preferred. The quaternary ammonium halide which is used in combination with palladium catalyst include tetraalkylammonium halide or tetraalkylphosphonium halide, such as the chlorides and bromides and particularly the bromides. Alkyl groups of the alkyl ammonium halides are primary and secondary alkyl groups containing about 1-8 carbon atoms. Tetra-n-butylammonium bromide is particularly preferred.

Cobalt (II) salts which can be used in making the inorganic cocatalyst employed in the practice of the present invention are for example, halides, and carboxylates, for example, Cobalt (II) chloride or Cobalt (II) acetate. Cobalt (II) acetate is preferred. Materials which are capable of forming pentadentate ligand with the cobalt (II) salt are for example, aromatic amines, such as bipyridines, pyridines, terpyridines, quinolines, isoquinolines and biquinolines; aliphatic amines, such as ethylene diamine and tetraalkylethylenediamine; aromatic ethers, such as crown ethers; aromatic or aliphatic amine ethers, such as cryptanes; and Schiff bases, such as di-(salicylal)-3,3'-diamino-N-methyldipropylamine.

Schiff bases are the preferred material for making the pentadentate ligand to form the inorganic cocatalyst of the present invention. The procedure of R. S. Drago et al, J. Am. Chem. Soc. 1985, 107, 2903 and Drago et al "Coordination Chemistry Review", 79 (1987) 321 can be used.

If desired, organic cocatalyst can be used in combination with the inorganic cobalt (II) cobalt complex. These organic cocatalysts are for example, quinones and aromatic diols formed by the reduction of said quinones, or a mixture thereof. 1,4-benzoquinone and hydroquinone have been found to be effective. In addition, compounds, such as 1,2-quinone and catechol, anthroquinone, 9,10-dihydroxy anthracene, phenanthroquinone also can be used.

Aromatic organic amines are the preferred organic cocatalyst which can be utilized in the practice of the present invention and are selected from the class consisting of terpyridines, phenanthrolines, and quinolines. More particularly there can be used terpyridine compounds, such as 2,2':6',2"-terpyridine, 2,2':6',2"-4'-thiomethylterpyridine and 2,2':6',2"'-4-terpyridine-N-oxide. In addition to terpyridine compounds, phenanthrolines also can be used such as, 1,10-phenanthrolines, 2,4,7,8-tetramethyl-1,10-phenanthroline, 4,7-diphenyl-1,10-phenanthroline and 3,4,7,8-tetramethyl-1,10-phenanthroline.

An effective amount of the palladium catalyst is, for example, an amount sufficient to provide about 1 gram-atom of palladium, per 800–10,000 and preferably 2,000–5,000 moles of organic hydroxy compound. The other components of the palladium catalyst are, for example, per gram-atom of palladium, about 0.1–5.0, preferably about 0.5–1.5 gram-atoms of cobalt, and about 5 to 150 and preferably about 20–50 moles of the tetraalkylammonium halide and about 0.1–3 and preferably about 0.3–1 moles of organic cocatalyst and/or reduction product thereof.

Solid drying agents, such as molecular sieves, can be used to improve yields. In some instances, carbon dioxide also can be used as a dessicant as taught in copending application Ser. No. 07/503,404, filed Apr. 2, 1990.

In order that those skilled in the art will be better able to practice a preferred form of the present invention, reference is made to the drawing. The drawing shows a schematic of a gas flow reactor system for preparing aromatic organic carbonate capable of delivering in a continuous manner, flow rate of about 50 ml to 1,000 ml, and preferably about 300 ml to 600 ml, a mixture of carbon monoxide and oxygen maintained at a substantially constant molar ratio and partial pressures.

More particularly, there is shown at 10 a carbon monoxide gas inlet and at 11, an oxygen inlet. 12 is a manifold vent, and 13 is an optional inlet for a gas, such as carbon dioxide. The reaction mixture can be fed into a low pressure reservoir at 20, or a high pressure reservoir at 21 which can be operated at a higher pressure than the reactor for the duration of the run. At 22 there is shown a reservoir outlet and at 23 an reservoir inlet. The gas feed pressure can be adjusted to about 50 psi over the desired reactor pressure at a reducing pressure regulator at 30. The gas can be further purified in scrubber 31 and then fed into a mass flow controller at 32 to allow for flow rates of from 1 to 1000 ml/min STP. The reactor feed gas can be heated in an oil bath at 33 having appropriate conduit means prior to being introduced to the reactor at 40. The reactor pressure can be controlled through manipulation of a back pressure regulator at 41. The reactor gas effluent may be either sampled for further analysis at 42 or vented to the atmosphere at 50. The reactor liquid can be sampled at 43. 45 is a condenser. An additional vent at 44 can allow for further system control, but is typically closed during the gas flow reaction.

In the practice of one form of the invention, the palladium catalyst, cocatalyst package, and organohydroxy compound are charged to the reactor. The reactor is sealed. Carbon monoxide and oxygen are introduced into an appropriate reservoir within proportions previously defined, until a suitable pressure such as 2800 psi is achieved.

Circulation of condenser water is initiated and the oil bath temperature can be raised to 100° C. Conduit between the oil bath and the reactor can be heated to a suitable temperature such as 100° C. The mass flow bypass can be opened and an appropriate accumulator valve can be opened and the reducing pressure regulator can be used to adjust the pressure. The reactor pressure can be further adjusted by the back pressure regulator. The mass flow bypass can be closed and the flow can be adjusted using the mass flow controller. Agitation of the reaction ingredients can be initiated once the reactor temperature is raised sufficiently to minimize the presence of solids such as phenol. Upon reaching a desirable reactor temperature, such as 100° C., aliquots can be taken to monitor the reaction.

In order that those skilled in the art will be better able to practice the present invention, the following examples are given by way of illustration and not by way of limitation. All parts are by weight unless otherwise indicated.

EXAMPLE 1

There was added into a 300 ml 316 SS Parr autoclave, 36.41 g (600 mmol) of phenol, 1.16118 g (5 mmol) of tetrabutylammonium bromide, 26.8 mg (0.12 mmol or 203 ppm of palladium) of palladium diacetate, 9.6 mg (0.04 mmol) of terpyridine, 24.6 mg (0.06 mmol) of "CoSMDPT" or cobalt di-(salicylal)-3,3'-diamino-N-methyldipropylamine and 5.01 g (30 mmol) of diphenyl ether as an internal standard for determination of diphenyl carbonate production by GC analysis. The reactor was sealed and flushed three times with carbon monoxide at 400 psi. The reactor vessel was then charged with oxygen (110 psi) and carbon monoxide (590 psi) at 30° C. The vessel was heated to 115° C. with rapid stirring of the solution (500 rpm) over the course of the reaction, during heat-up and cool-down. Aliquots were taken at predetermined times for GC analysis to access the amount of diphenyl carbonate which had been produced.

The same procedure was repeated except that in place of the CoSMDPT, there was utilized 0.06 mmol of cobalt diacetate.

After a 3½ hour reaction period, the following results were obtained where CoSMDPT is the cobalt pentadentate catalyst:

TABLE 1

| Inorganic Co-Catalyst | % DPC 3.5 hr | moles DPC/liter-hr 3.5 hr |
| --- | --- | --- |
| Co(OAc)$_2$ | 13.4 | 0.17 |

TABLE 1-continued

| Inorganic Co-Catalyst | % DPC 3.5 hr | moles DPC/liter-hr 3.5 hr |
|---|---|---|
| CoSMDPT* | 23.6 | 0.35 |

*CoSMDPT = Cobalt di(salicylal)-3,3'-diamino-N-methyldipropylamine (4)

The above results show that the cobalt pentadentate organic cocatalyst provides a faster diphenyl carbonate production rate as compared to the use of the cobalt diacetate catalyst.

EXAMPLE 2

A series of reactions utilizing the constant composition gas flow reactor shown by the drawing were performed to further evaluate the effectiveness of the cobalt complex containing the pentadentate Schiff base as an inorganic cocatalyst for palladium in the direct carbonylation of phenol. There was added to the flow reactor, 60.9900 g (648 mmol) of phenol, 4.0700 g (12.62 mmol) of tetrabutylammonium bromide, 0.1218 g (0.2967 mmol) of CoSMDPT, and 0.0660 g (2940 mmol; 479 ppmpd) of palladium diacetate. There was also introduced into the reactor 26.07 g of molecular sieves (4 Angstrom) which had been activated overnight at 300° C. The molecular sieves were contained in a perforated Teflon resin basket mounted to the stir shaft above the liquid level of the reaction mixture and were used as a dessicant. The reaction vessel was sealed. The constant flow reactor system was then charged to a total pressure 2800 psi including 2600 psi of carbon monoxide (7.1% oxygen in carbon monoxide) and 200 psi of oxygen. The reactor was then heated to a temperature of 115° C. and the pressure was set to 1650 psi. The gas reservoir was then opened to the reactor solution followed by opening the reactor outlet to permit gas flow through the reactor solution. The reactor pressure was adjusted to 1600 psi and there was introduced a flow of 350 ml/min STP of the mixture of oxygen and carbon monoxide. Stirring was initiated at 570–620 rpm as soon as the reactor temperature reached 40° C. Upon reaching the reacted temperature of 115° C., aliquots were taken periodically for GC analysis to quantify the amount of diphenyl carbonate produced.

At 0.0 hr, the yield of diphenyl carbonate was 0.336 g (4.83%). At 1.00 hr, the yield of diphenyl was 13.4 g (19.25%). At 2.00 hr, the yield of diphenyl carbonate was 20.3 g (29.24%). At 7.00 hr, the yield of diphenyl carbonate was 28.7 g (41.28%).

The same procedure was repeated except that in one instance 0.0354 g (0.1517 mmol) of 2,2':2',6''-terpyridine was added to the mixture as an organic cocatalyst. An additional reaction was run following the same procedure except that 0.0564 g (0.3186 mmol) of cobalt diacetate was substituted for the CoSMDPT along with 2,2':2',6''-terpyridine (0.0354 g, 0.1517 mmol) was as an organic cocatalyst. The following results were obtained after a 2 hour reaction run:

TABLE 2

| Inorganic Co-Catalyst | Organic Co-Catalyst | % DPC 2 Hr | moles DPC/liter-hr 2 Hr |
|---|---|---|---|
| Co(OAc)₂ | None | 6.2 | 0.17 |
| CoSMDPT* | None | 29.2 | 0.80 |
| Co(OAc)₂ | Terp** | 23.5 | 0.61 |
| CoSMDPT* | Terp** | 45.0 | 1.19 |

*CoSMDPT = Cobalt di-(salicylal)-3,3'-diamino-N-methyldipropylamine (4)
**Terp = 2,6',2',6''-terpyridine The above results clearly demonstrate the beneficial use of cobalt pentadentate Schiff base complexes as inorganic cocatalyst in a direct carbonylation of phenol to diphenyl carbonate. Optimization of the reaction conditions outlined above and/or further refinement of the relative catalyst loadings concentrations would greatly improve both the yield and the rate of diphenyl carbonate production. It was further found that the selectivity between diphenyl carbonate and phenyl salicylate formation and selectivity between diphenyl carbonate and carbon dioxide formation was comparable to or better than that found with cobalt diacetate as an inorganic cocatalyst.

Although the above examples are directed to only a few of the very many variables which can be utilized in the practice of the method of the present invention, it should be understood that the present invention is directed to the use of a much broader variety of materials capable of forming ligands with the cobalt (II) salts as well as organic cocatalyst which can be utilized in combination with such cobalt pentadentate complexes as set forth in the description preceding these examples.

What is claimed is:

1. A method for making aromatic organic carbonate comprising heating to a temperature of about 60° C. to about 150° C. a mixture comprising aromatic organic hydroxy compound, carbon monoxide, oxygen, and an effective amount of a palladium carbonylation catalyst comprising,
   (a) catalytically active palladium in the metallic or chemically combined state,
   (b) an inorganic cocatalyst in the form of a cobalt complex of a cobalt (II) salt and a Schiff base, and
   (c) a quaternary ammonium or phosphonium halide.

2. A method in accordance with claim 1, wherein the aromatic organic carbonate is diphenylcarbonate.

3. A method in accordance with claim 1 wherein the cobalt complex is cobalt di(salicylal)-3,3'-diamino-N-methyldipropylamine.

4. A method in accordance with claim 1, where there is used a terpyridine compound in combination with a cobalt complex of a cobalt (II), salt and a Schiff base as part of the palladium carbonylation catalyst.

* * * * *